(12) United States Patent
Kamon

(10) Patent No.: US 11,954,897 B2
(45) Date of Patent: Apr. 9, 2024

(54) MEDICAL IMAGE PROCESSING SYSTEM, RECOGNITION PROCESSING PROCESSOR DEVICE, AND OPERATION METHOD OF MEDICAL IMAGE PROCESSING SYSTEM

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 78 days.

(21) Appl. No.: 17/938,609

(22) Filed: Oct. 6, 2022

(65) Prior Publication Data

US 2023/0037178 A1 Feb. 2, 2023

Related U.S. Application Data

(63) Continuation of application No. PCT/JP2021/007918, filed on Mar. 2, 2021.

(30) Foreign Application Priority Data

Apr. 8, 2020 (JP) ................................ 2020-069714

(51) Int. Cl.
*G06V 10/70* (2022.01)
*G06T 7/00* (2017.01)
*H04N 5/268* (2006.01)

(52) U.S. Cl.
CPC ............ *G06V 10/70* (2022.01); *G06T 7/0012* (2013.01); *H04N 5/268* (2013.01); *G06T 2207/10016* (2013.01); *G06T 2207/30004* (2013.01)

(58) Field of Classification Search
CPC ................ G06V 10/70; G06V 2201/03; G06T 2207/10016; G06T 2207/10068;
(Continued)

(56) References Cited

U.S. PATENT DOCUMENTS

| 2015/0145979 A1 | 5/2015 | Tashiro et al. |
| 2016/0157787 A1 | 6/2016 | Merritt et al. |

(Continued)

FOREIGN PATENT DOCUMENTS

| JP | 2011-87827 A | 5/2011 |
| JP | 2015-112429 A | 6/2015 |

(Continued)

OTHER PUBLICATIONS

International Search Report issued in PCT/JP2021/007918; dated Apr. 27, 2021.

(Continued)

*Primary Examiner* — Sherrie Hsia
(74) *Attorney, Agent, or Firm* — Studebaker & Brackett PC

(57) ABSTRACT

An endoscope processor device generates first video signals. A recognition processing processor device generates second video signals by reflecting a result of recognition processing based on the first video signals. A display displays any one of the second video signals or the first video signals switched from the second video signals on the basis of first video switching signals from the recognition processing processor device. The display displays that a result display of the recognition processing is being stopped in a case where the result display of the recognition processing by the second video signals is stopped.

11 Claims, 7 Drawing Sheets

(58) Field of Classification Search
CPC ........ G06T 2207/30004; G06T 7/0012; H04N 5/268; H04N 23/555; G16H 30/40; A61B 1/0005; A61B 1/0638; A61B 1/000096; A61B 1/00055; A61B 1/000094
USPC .............................. 348/45, 65, 69; 382/128
See application file for complete search history.

(56) References Cited

U.S. PATENT DOCUMENTS

| | | |
|---|---|---|
| 2016/0261846 A1 | 9/2016 | Kasumi et al. |
| 2018/0242817 A1 | 8/2018 | Imaizumi et al. |
| 2020/0069160 A1 | 3/2020 | Oosake |
| 2020/0077869 A1 | 3/2020 | Ida |
| 2020/0193236 A1 | 6/2020 | Oosake |
| 2020/0268471 A1* | 8/2020 | Kajita .................... A61B 90/50 |

FOREIGN PATENT DOCUMENTS

| | | |
|---|---|---|
| JP | 2017-536213 A | 12/2017 |
| JP | 2018-139848 A | 9/2018 |
| KR | 10-2020-0027202 A | 3/2020 |
| WO | 2014/192689 A1 | 12/2014 |
| WO | 2017/073338 A1 | 5/2017 |
| WO | 2018/221033 A1 | 12/2018 |
| WO | 2019/054045 A1 | 3/2019 |

OTHER PUBLICATIONS

International Preliminary Report on Patentability (Chapter I) and Written Opinion of the International Searching Authority issued in PCT/JP2021/007918; dated Oct. 6, 2022.

The extended European search report issued by the European Patent Office dated Aug. 30, 2023, which corresponds to European Application No. 21784237.6-1126 and is related to U.S. Appl. No. 17/938,609.

* cited by examiner ically intelligence (AI).
MEDICAL IMAGE PROCESSING SYSTEM, RECOGNITION PROCESSING PROCESSOR DEVICE, AND OPERATION METHOD OF MEDICAL IMAGE PROCESSING SYSTEM

CROSS-REFERENCE TO RELATED APPLICATIONS

This application is a Continuation of PCT International Application No. PCT/JP2021/007918 filed on 2 Mar. 2021, which claims priority under 35 U.S.C § 119(a) to Japanese Patent Application No. 2020-069714 filed on 8 Apr. 2020. The above application is hereby expressly incorporated by reference, in its entirety, into the present application.

BACKGROUND OF THE INVENTION

1. Field of the Invention

The present invention relates to a medical image processing system, a recognition processing processor device, and an operation method of a medical image processing system which use recognition processing such as artificial intelligence (AI).

2. Description of the Related Art

In the current medical field, a medical image processing system using a medical image, such as an endoscope system comprising a light source device, an endoscope, and a processor device is widespread. Further, in recent years, a function of detecting a region-of-interest from a medical image such as an endoscopic image by recognition processing such as artificial intelligence (AI) (for example, WO2017/073338A1, corresponding to US2018/0242817A) and a diagnosis support function of classifying lesion types are used. Such a diagnosis support function is expected to lead to prevention of overlooking of lesions and reduction of burden on users.

SUMMARY OF THE INVENTION

In order to realize the above-described diagnosis support function, it is conceivable that video signals from a medical image processor device that processes a medical image such as an endoscopic image are transmitted to a recognition processing processor device connected to the medical image processor device and recognition processing is performed by the recognition processing processor device. A result of the recognition processing in the recognition processing processor device is subjected to emphasizing processing or the like of the region-of-interest to be displayed on a display.

However, there may be a case where a delay in the recognition processing may adversely affect the operation of a user, or a case where the video signals are not appropriately displayed on the display due to a failure of the recognition processing processor device. There has been a demand for stable video display without a delay that would cause such a situation.

JP2011-87827A discloses that, in a case where an abnormality relating to second video signals recorded in a filing device is not detected, the second video signals (PC standard video signals) are displayed, and in a case where the abnormality is inspected, first video signals (TV standard video signals) are displayed. However, JP2011-87827A does not contain a description relating to an abnormality in the recognition process.

An object of the present invention is to provide a medical image processing system, a recognition processing processor device, and an operation method of a medical image processing system which can perform stable video display without a delay due to recognition processing in a case where the recognition processing is performed on the basis of medical images.

A medical image processing system of the present invention includes a first processor that sequentially acquires medical images, and generates first video signals from the medical images; a second processor that receives the first video signals from the first processor, performs recognition processing on the first video signals, and performs processing for recognition processing for displaying a result of the recognition processing on the first video signals to generate second video signals; and a display, in which the second processor generates first video switching signals, and the display displays any one of the second video signals or the first video signals switched from the second video signals on the basis of the first video switching signals, and displays that a result display of the recognition processing is being stopped in a case where the result display of the recognition processing by the second video signals is stopped.

It is preferable that the medical image processing system further includes a third processor provided in the display, in which the display receives the first video signals from the first processor, and receives the second video signals from the second processor, and in a case where the display displays the second video signals, the third processor switches the display on the display from the second video signals to the first video signals on the basis of the first video switching signals.

It is preferable that in a case where the first video switching signals are received from the second processor, the first processor transmits first video priority signals for displaying the first video signals with priority over the second video signals, to the display, the display receives any one of the first video signals or the first video priority signals from the first processor, and receives the second video signals from the second processor, and in a case where the display displays the second video signals, the display on the display is switched from the second video signals to the first video signals on the basis of the first video priority signals.

It is preferable that in a case where the display is switched from the second video signals to the first video signals on the basis of the first video priority signals, the first processor generates stop-display-processed first video signals obtained by performing stop display processing on the first video signals, and transmits the stop-display-processed first video signals to the display as the first video signals.

It is preferable that the second processor transmits the second video signals to the display in a case where it is determined that the recognition processing is being executed on the basis of the first video switching signals, and transmits the first video signals to the display in a case where it is determined that the recognition processing is being stopped on the basis of the first video switching signals, the second video signals are displayed on the display in a case where the second video signals are transmitted from the second processor to the display, and the first video signals are displayed on the display in a case where the first video signals are transmitted from the second processor to the display.

It is preferable that in a case where the first video signals are displayed on the display on the basis of the first video switching signals, the second processor generates stop-display-processed first video signals obtained by performing stop display processing on the first video signals, and transmits the stop-display-processed first video signals to the display as the first video signals.

It is preferable that the second processor stops the recognition processing according to at least one of a stop input for the recognition processing by a user, the recognition process being in an abnormal state, or an operation status by the user being a specific operation status so that the result display of the recognition processing is stopped. It is preferable that the specific operation status includes a treatment operation of the user using a treatment tool. It is preferable that the second processor generates second video switching signals in a case where the recognition processing is restarted, and the display displays the second video signals switched from the first video signals by the second video switching signals.

A recognition processing processor device according to the present invention is connected to a first processor sequentially acquiring medical images and generating first video signals from the medical images, and is connected to a display, and the recognition processing processor device includes a second processor that receives the medical images from the first processor, performs recognition processing on the first video signals, and performs processing for recognition processing for displaying a result of the recognition processing on the first video signals to generate second video signals, in which the second processor generates first video switching signals, and the any one of the second video signals or the first video signals switched from the second video signals on the basis of the first video switching signals is displayed on the display, and a fact that a result display of the recognition processing is being stopped is displayed on the display in a case where the result display of the recognition processing by the second video signals is stopped.

In an operation method of a medical image processing system according to the present invention, the medical image processing system includes a first processor that sequentially acquires medical images, and generates first video signals from the medical images, a second processor that receives the first video signals from the first processor, performs recognition processing on the first video signals, and performs processing for recognition processing for displaying a result of the recognition processing on the first video signals to generate second video signals, and a display, and the operation method includes causing the second processor to generate first video switching signals; and causing the display to displays any one of the second video signals or the first video signals switched from the second video signals on the basis of the first video switching signals, and to display that a result display of the recognition processing is being stopped in a case where the result display of the recognition processing by the second video signals is stopped.

According to the present invention, in a case where recognition processing is performed on the basis of medical images, it is possible to perform stable video display without a delay due to the recognition processing.

DESCRIPTION OF THE PREFERRED EMBODIMENTS

First Embodiment

Figure 1:
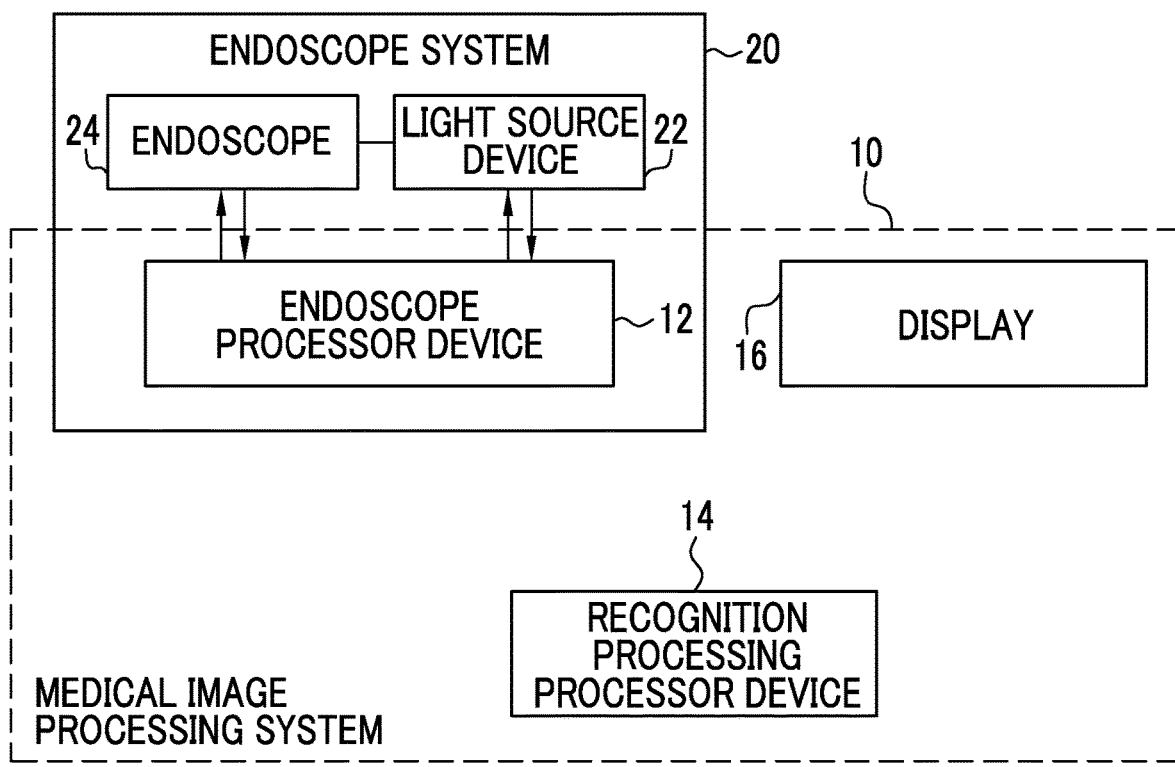
FIG. 1 is a block diagram illustrating functions of an endoscope system and a medical image processing system.

As illustrated in FIG. 1, a medical image processing system 10 of a first embodiment includes an endoscope processor device 12, a recognition processing processor device 14 (recognition processing image processing device), and a display 16.

The endoscope processor device 12 is provided inside an endoscope system 20. The endoscope system 20 includes a light source device 22 and an endoscope 24 in addition to the endoscope processor device 12. The light source device 22 supplies illumination light to be emitted to a subject, to the endoscope 24. The endoscope 24 acquires an endoscopic image by irradiating the subject with at least one of light in a white wavelength range or light in a specific wavelength range to image the subject. The light in a specific wavelength range used as the illumination light by the endoscope 24 is, for example, light in a wavelength range shorter than a green wavelength range, particularly light in a blue band or a violet band in the visible range.

The endoscope processor device 12 sequentially acquires endoscopic images from the endoscope 24, and generates first video signals from the acquired endoscopic images. The first video signals are signals to be displayed on the display 16. The first video signals are transmitted to at least the recognition processing processor device 14. In a case where a display (not illustrated) for an endoscope is provided in the endoscope system 20, the first video signals may be transmitted to the display for the endoscope, and the first video signals may be displayed on the display for the endoscope.

In the present embodiment, the endoscope processor device 12 that acquires the endoscopic image from the endoscope 24 will be described as an example, but in addition to the endoscope processor device 12, the invention can be applied to a medical image processing device that acquires various medical images and performs an image processing. The medical image is a still image or a motion picture (so-called examination motion picture). In a case where the medical image is a motion picture, frame images constituting the motion picture can be acquired as still images after examination. Further, in a case where the medical image is a motion picture, displaying the medical image includes displaying the still image of one representative frame constituting the motion picture, and reproducing the motion picture one or a plurality of times. In addition, the medical image includes an image captured by a doctor using a medical apparatus of the medical image processing device, and an image automatically captured by the medical apparatus of the medical image processing device without an imaging instruction of the doctor.

In a case where a plurality of medical images can be acquired, the medical image processing device can selectively acquire one or a plurality of medical images among the medical images. Further, the medical image processing device can acquire a plurality of medical images acquired in a plurality of different examinations. For example, one or both of the medical image acquired by the examination performed in the past and the medical image acquired by the latest examination can be acquired. That is, the medical image processing device can arbitrarily acquire the medical image.

The recognition processing processor device 14 receives the first video signals from the endoscope processor device 12, performs recognition processing on the first video signals, and performs processing for recognition processing for displaying the result of the recognition processing on the first video signals to generate second video signals. Further, the recognition processing processor device 14 generates first video switching signals in a case where the recognition processing is stopped.

The display 16 displays any one of the second video signals from the recognition processing processor device 14 or the first video signals switched from the second video signals by the first video switching signals, and displays that the result display of the recognition processing is stopped in a case where the result display of the recognition processing by the second video signals is stopped in the recognition processing processor device 14. As the case where the result display of the recognition processing is stopped, a case where the result display of the recognition processing is stopped because the recognition processing is stopped, and a case where only the result display of the recognition processing is stopped while the recognition processing itself is being executed are included.

Figure 2:
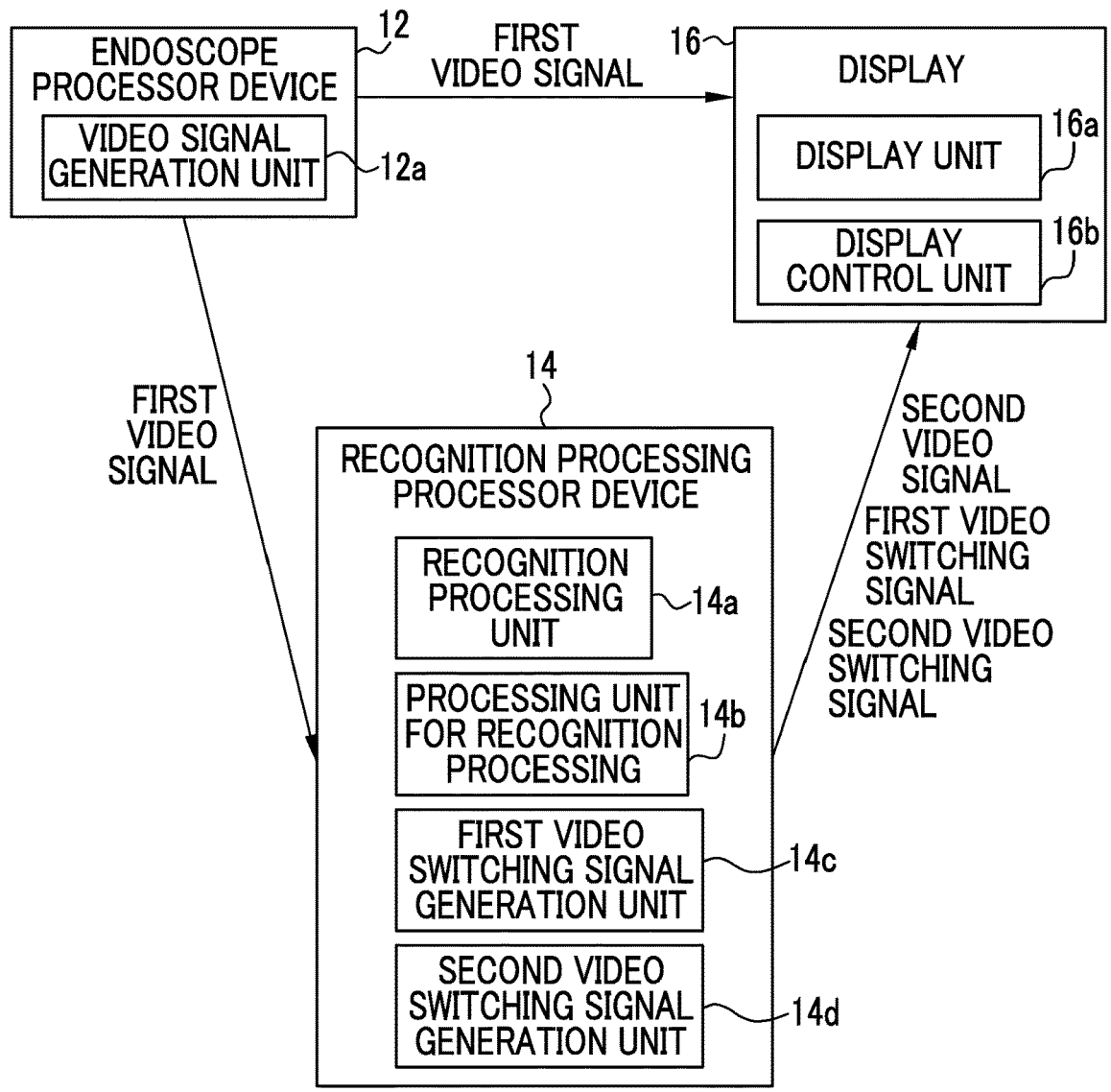
FIG. 2 is a block diagram illustrating a function of a medical image processing system of a first embodiment.

Hereinafter, the details of the switching display between the second video signals and the first video signals in a case where the recognition processing is stopped will be described with reference to FIG. 2. The endoscope processor device 12 has a video signal generation unit 12a that generates first video signals from the medical image. The recognition processing processor device 14 includes a recognition processing unit 14a, a processing unit for recognition processing 14b, a first video switching signal generation unit 14c that generates first video switching signals, and a second video switching signal generation unit 14d that generates second video switching signals. The display 16 includes a display unit 16a, and a display control unit 16b that performs display control of the display unit 16a. In FIG. 2, an input unit to the display 16 has two systems of an input from the endoscope processor device 12 and an input from the recognition processing processor device 14, but the input unit to the display 16 may use one system by integrating the input from the endoscope processor device 12 and the input from the recognition processing processor device 14 using a mixer.

In the endoscope processor device 12, a first program relating to generation processing of the first video signals is incorporated in a first program memory (not illustrated). The function of the video signal generation unit 12a is realized by operating the first program by a first control unit (not illustrated) configured by a first processor. In the recognition processing processor device 14, a second program relating to recognition processing and the like is incorporated in a second program memory (not illustrated). The functions of the recognition processing unit 14a, the processing unit for recognition processing 14b, the first video switching signal generation unit 14c that generates the first video switching signals, and the second video switching signal generation unit 14d that generates the second video switching signals are realized by operating the second program by a second control unit (not illustrated) configured by a second processor. In the display 16, the function of the display control unit 16b is realized by operating a third program relating to the display control by a third control unit (not illustrated).

In the endoscope processor device 12, the first video signals are generated from the medical image by the video signal generation unit 12a, and the generated first video signals are transmitted to the recognition processing processor device 14. In the recognition processing processor device 14, the recognition processing is performed on the basis of the first video signals by the recognition processing unit 14a. The recognition processing performed by the recognition processing unit 14a is preferably, for example, processing by a learning model obtained by learning using a neural network (NN), a convolutional neural network (CNN), AdaBoost, and random forest. That is, it is preferable to output the detection of the region-of-interest such as a lesion area in response to the input of the first video signals to the learning model. Further, as the recognition processing, the detection of the region-of-interest may be performed based on a feature amount obtained from color information of the first video signals, the gradient of pixel values, or the like. The gradient of the pixel values or the like is changed depending on, for example, the shape of the subject (global undulations of a mucous membrane or local depressions or bumps), color (color such as whitening due to inflammation, bleeding, redness, or atrophy), a feature of a tissue (thickness, depth, or density of a blood vessel, or a combination thereof), or a feature of a structure (pit pattern or the like).

Further, the region-of-interest detected in the recognition processing is a region including a lesion area represented by a cancer, a treatment trace, a surgical scar, a bleeding site, a benign tumor area, an inflammation area (including a portion with changes such as bleeding or atrophy in addition to a so-called inflammation), a cauterization scar due to heating or a marking area marked by coloring with a coloring agent, a fluorescent drug, or the like, or a biopsy area where biopsy examination (so called biopsy) is performed. That is, a region including a lesion, a region having a possibility of a lesion, a region where any treatment such as a biopsy is performed, a treatment tool such as clips or forceps, a region which is required to be observed in detail regardless of a possibility of a lesion, such as a dark region (back of folds, a region where observation light is difficult to reach due to the depth of the lumen), or the like can be a region-of-interest. The recognition processing detects a region including at least one of a lesion area, a treatment trace, a surgical scar, a bleeding site, a benign tumor area, an inflammation area, a marking area, or a biopsy area, as the region-of-interest.

Figure 3:
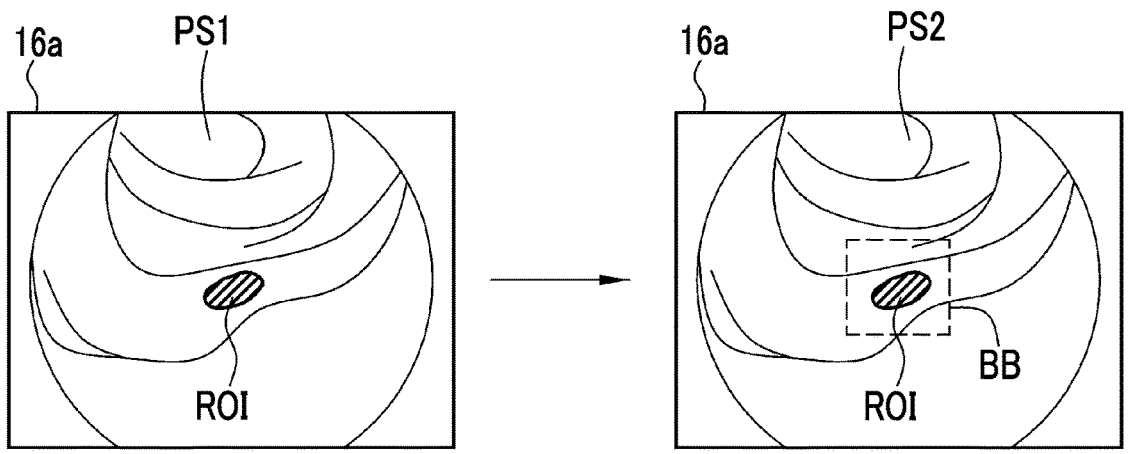
FIG. 3 is an explanatory diagram illustrating processing for recognition processing.

The processing unit for recognition processing 14b performs the processing for recognition processing on the first video signals on the basis of the result of the recognition processing to generate the second video signals. Specifically, in a case where the detection of the region-of-interest is performed as the recognition processing, as illustrated in FIG. 3, processing of adding a bounding box BB surrounding a region-of-interest ROI to first video signals PS1 is performed as the processing for recognition processing. As a result, second video signals PS2 are obtained. The second video signals are transmitted to the display 16. In the display 16, the bounding box BB surrounding the region-of-interest ROI is displayed as the result display of the recognition processing.

The first video switching signal generation unit 14c generates the first video switching signals for switching the display on the display 16 from the second video signals to the first video signals. The first video switching signals are used for not displaying the result of the recognition processing on the display 16, by switching the display on the display 16 to the first video signals in which the result of the recognition processing is not reflected in a case where the recognition processing is stopped by an instruction from a user or the like. The first video switching signals are transmitted to the display 16. The first video switching signals are generated and transmitted to the display 16 only in a case where the recognition processing is stopped, and the first video switching signals include two kinds of signals of OFF signals and ON signals so that the OFF signals that do not switch the display between the second video signals and the first video signals are continuously transmitted to the display 16 in a case where the recognition processing is not stopped, and the ON signals that switch the display between the second video signals and the first video signals are transmitted to the display 16 in a case where the recognition processing is stopped.

The second video switching signal generation unit 14d generates the second video switching signals for switching the display on the display 16 from the first video signals to the second video signals. The second video switching signals are used for restarting the recognition processing on the display 16 by switching the display in the display 16 to the second video signals in which the result of the recognition processing is reflected in a case where the recognition processing is restarted by an instruction from a user or the like, even in a case where the first video signals are being displayed on the display 16 on the basis of the first video switching signals. The second video switching signals are transmitted to the display 16.

Figure 4:
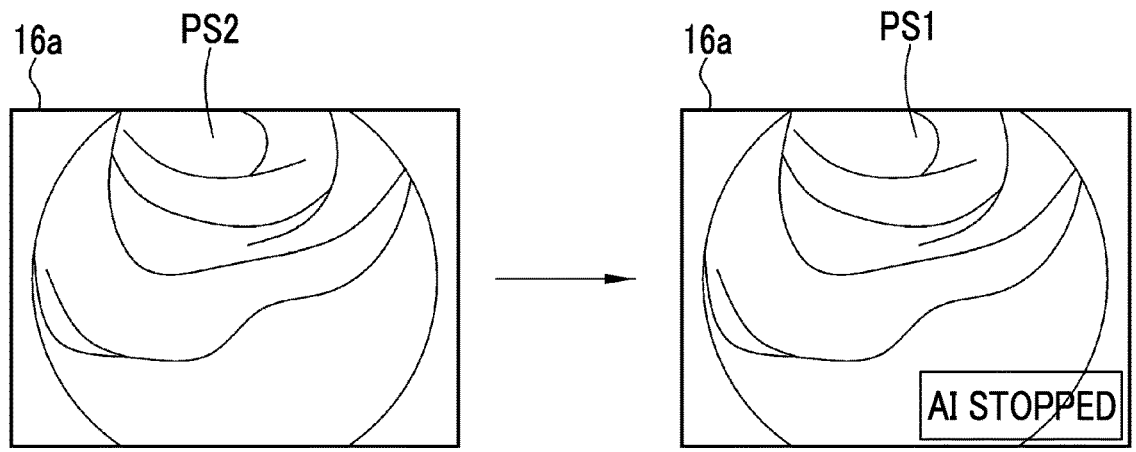
FIG. 4 is an explanatory diagram illustrating switching of display from second video signals to first video signals.

In the display 16, the display control unit 16b displays the second video signals in which the result of the recognition processing is reflected on the display unit 16a in a case where switching the display between the first video signals and the second video signals is not performed on the basis of the first video switching signals. On the other hand, in a case where switching the display between the first video signals and the second video signals is performed on the basis of the first video switching signals, the display control unit 16b switches the image display on the display unit 16a from the display of the second video signals to the display of the first video signals according to a display switching instruction based on the first video switching signals, as illustrated in FIG. 4. In this case, the display unit 16a also displays that the result display of the recognition processing is being stopped ("AI stopped"). Further, as the display of the result display of the recognition processing is being stopped, displaying that the execution of the processing for recognition processing is being stopped may be used in addition to the display of "AI stopped".

In the present embodiment, since the first video signals and the second video signals are switched and displayed on the display 16, it may be difficult for a user to grasp whether or not the recognition processing is being executed. For example, even though the region-of-interest ROI is displayed on the display 16, in a case where the bounding box BB is not displayed (refer to FIG. 3), the user cannot determine whether or not the recognition processing has not been executed or the recognition processing has not been able to detect the region-of-interest ROI in terms of performance. In a case where the recognition processing is stopped without the user's intention, the support function does not work so that there may be a risk that the region-of-interest is overlooked. Therefore, the above risk can be reduced by displaying whether or not the result display of the recognition processing, such as "AI stopped" described above is made on the display 16. In FIG. 4, the fact that the result display of the recognition processing is being stopped is displayed with character information, but may be displayed with graphic information, or a configuration may be used in which a display format of the entire region of displaying the image on the display 16 is switched.

Note that "AI" in FIG. 4 represents artificial intelligence using a learning model. Further, the information relating to the fact that the recognition processing is being stopped is included in the first video switching signals, and is preferably displayed on the first video signals in a superimposed manner.

Figure 5:
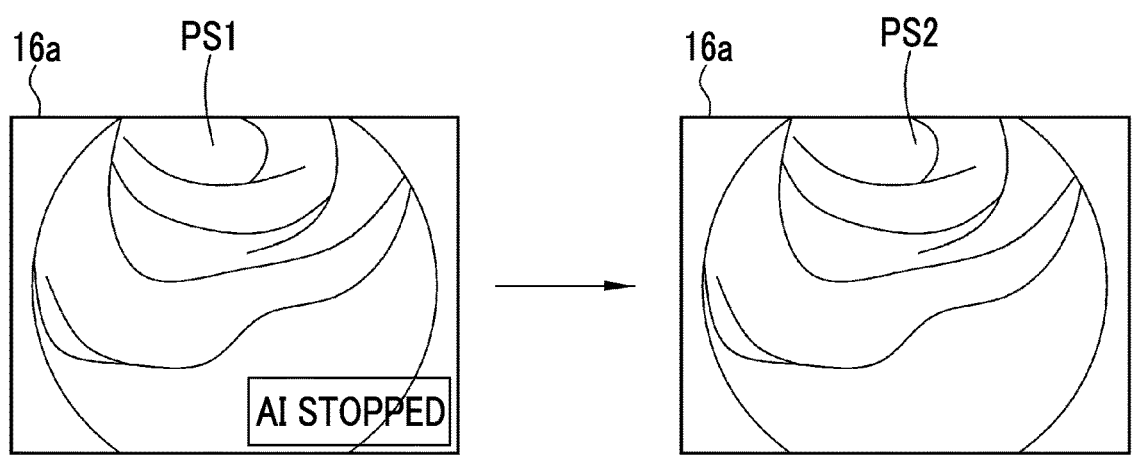
FIG. 5 is an explanatory diagram illustrating switching of display from first video signals to second video signals.

Further, in a case where switching the display between the first video signals and the second video signals is performed on the basis of the second video switching signals, the display control unit 16b switches the image display on the display unit 16a from the display of the first video signals to the display of the second video signal according to a display switching instruction based on the second video switching signals, as illustrated in FIG. 5. In this case, the display of the first video signals is switched to the display of the second video signals, so that the display indicating that the result display of the recognition processing is being stopped ("AI stopped") is turned off.

Figure 6:
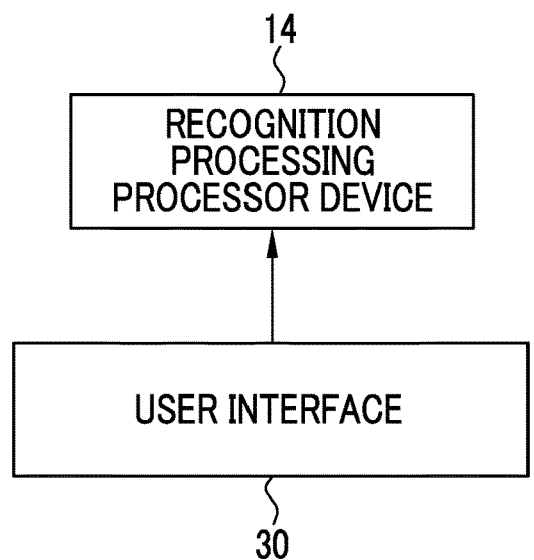
FIG. 6 is a block diagram illustrating a user interface.

In the recognition processing processor device 14, in a case where the recognition processing is stopped, the result display of the recognition processing is preferably stopped by stopping the recognition processing according to at least one of a stop input for the recognition processing by the user, the recognition process being in an abnormal state, or the operation status by the user being a specific operation status. In a case where the recognition processing is stopped by the stop input for the recognition processing by the user, the stop input is preferably performed using a user interface 30 connected to the recognition processing processor device 14 as illustrated in FIG. 6.

Note that a delay due to the time of recognition processing occurs in a case where the recognition processing is performed. Such a delay may adversely affect the user at a timing at which support by the recognition processing is not necessary. For example, the support function assuming the prevention of the overlooking is not necessary during the treatment work by a doctor as the user, and further, there is a possibility that the adverse effect due to the delay becomes large at a timing at which a delicate operation such as a treatment is required. Therefore, at such a timing, the user operates the user interface 30 to stop the recognition processing. Such a stop of the recognition processing can be realized not only in the first embodiment but also in second and third embodiments described later. While the recognition processing is stopped, the first video signals in which the result of the recognition processing is not reflected are displayed on the display. In the recognition processing processor device 14, the recognition processing is being stopped, but only the switching of the display from the second video signals to the first video signals may be performed without stopping the recognition processing.

Figure 7:
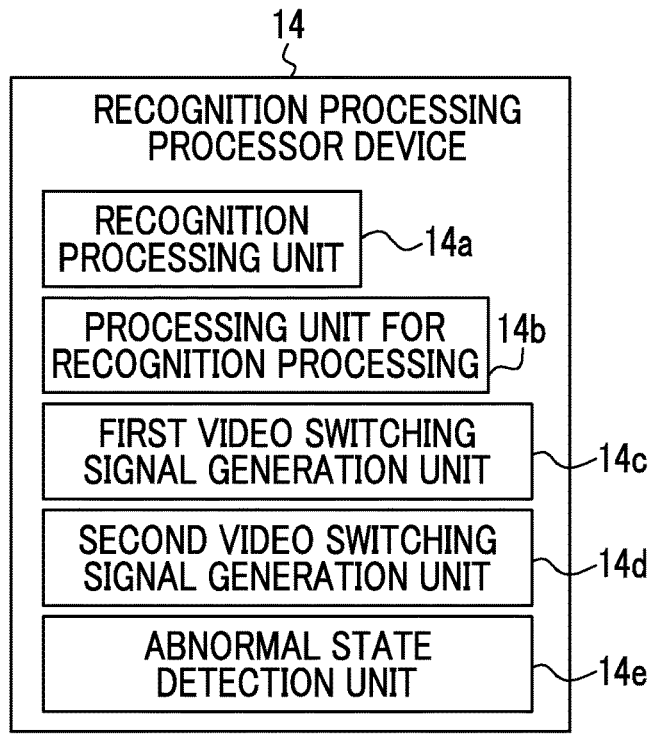
FIG. 7 is a block diagram illustrating an abnormal state detection unit.

In a case where the recognition processing is stopped according to the fact that the recognition processing is in the abnormal state, it is preferable to stop the recognition processing in a case where the abnormal state is detected by an abnormal state detection unit 14e provided in the recognition processing processor device 14, as illustrated in FIG. 7. Note that examples of the abnormal state include a failure of the recognition processing processor device 14 and the like.

Figure 8:
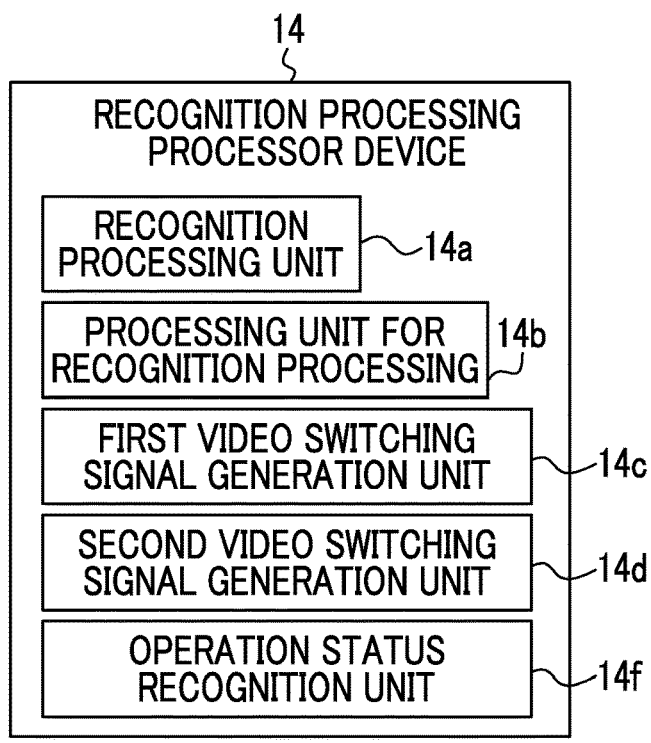
FIG. 8 is a block diagram illustrating an operation status recognition unit.

In a case where the recognition processing is stopped according to the fact that the operation status by the user is a specific operation status, it is preferable to stop the recognition processing in a case where the specific operation status is recognized by an operation status recognition unit 14f provided in the recognition processing processor device 14, as illustrated in FIG. 8. It is preferable that the specific operation status includes a treatment operation of the user using a treatment tool, such as excising a lesion area.

Second Embodiment

Figure 9:
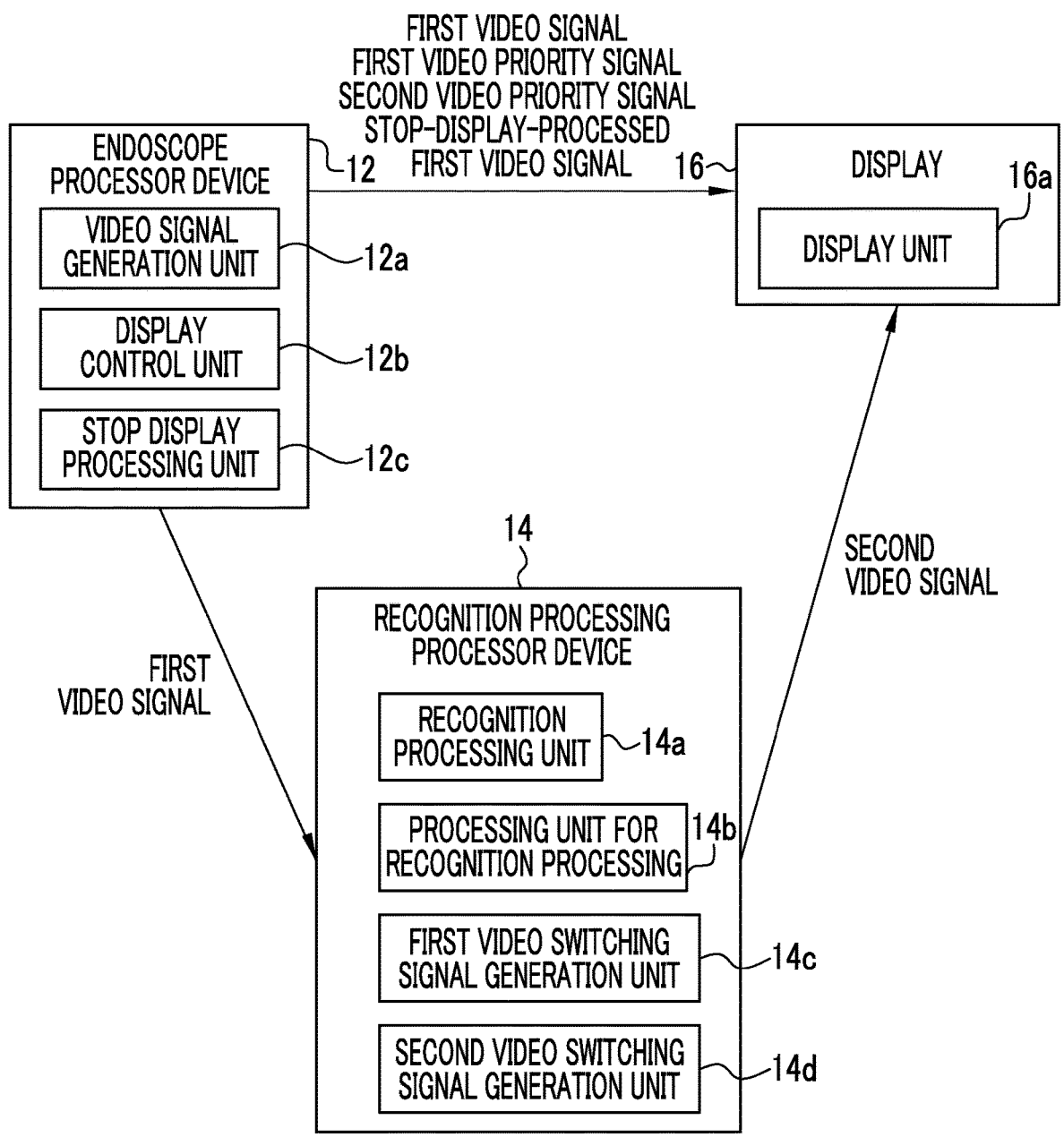
FIG. 9 is a block diagram illustrating a function of a medical image processing system of a second embodiment.

In the first embodiment, the first video switching signals are transmitted to the display 16, and the display between the first video signals and the second video signals on the display 16 is switched. However, in the second embodiment, the first video switching signals are transmitted to the endoscope processor device 12. In the second embodiment, as illustrated in FIG. 9, the endoscope processor device 12 includes the video signal generation unit 12a that generates the first video signals from the medical image, a display control unit 12b, and a stop display processing unit 12c. The recognition processing processor device 14 includes the recognition processing unit 14a, the processing unit for recognition processing 14b, the first video switching signal generation unit 14c that generates the first video switching signals, and the second video switching signal generation unit 14d that generates the second video switching signals. The display 16 includes the display unit 16a. The same reference numerals in the first embodiment and the second embodiment have substantially the same functions in the first embodiment and the second embodiment except for the first video switching signal generation unit 14c and the second video switching signal generation unit 14d. It is also preferable that the second embodiment also includes the user interface 30, the abnormal state detection unit 14e, and the operation status recognition unit 14f of the first embodiment.

In the second embodiment, the first video switching signal generation unit 14c transmits the first video switching signals to the endoscope processor device 12. Further, the second video switching signal generation unit 14d transmits the second video switching signals to the endoscope processor device 12. In the endoscope processor device 12, in a case where it is determined that the recognition processing is stopped on the basis of the first video switching signals from the recognition processing processor device 14, the display control unit 12b transmits first video priority signals for displaying the first video signals with priority over the second video signals on the display 16. Further, in a case where it is determined that the recognition processing is restarted on the basis of the second video switching signals from the recognition processing processor device 14, the display control unit 12b transmits second video priority signals for displaying the second video signals with priority over the first video signals on the display 16.

In the second embodiment, in the display 16, the second video signals in which the result of the recognition processing is reflected are displayed on the display unit 16a in a case where switching the display between the first video signals and the second video signals is not performed on the basis of the first video priority signals. On the other hand, in a case where switching the display between the first video signals and the second video signals is performed on the basis of the first video priority signals, the image display on the display unit 16a is switched from the display of the second video signals to the display of the first video signals according to a display switching instruction based on the first video switching signals (refer to FIG. 4). In this case, the display unit 16a also displays that the result display of the recognition processing is being stopped ("AI stopped").

Further, in a case where switching the display between the first video signals and the second video signals is performed on the basis of the second video priority signals, the display control unit 12b switches the image display on the display unit 16a from the display of the first video signals to the display of the second video signal according to a display switching instruction based on the second video priority signals (refer to FIG. 5). In this case, the display of the first video signals is switched to the display of the second video signals, so that the display indicating that the result display of the recognition processing is being stopped ("AI stopped") is turned off.

In the second embodiment, in a case where the first video signals are displayed on the display unit 16a according to a display switching instruction based on the first video switching signals, the stop display processing unit 12c provided in the endoscope processor device 12 performs stop display processing indicating that the recognition processing is being stopped on the first video signals to generate stop-display-processed first video signals. The stop-display-processed first video signals are transmitted to the display 16. In a case where the display of the second video signals is switched to the display of the first video signals on the basis of the first video priority signals, the display is switched to the display of the stop-display-processed first video signals.

Third Embodiment

In the first embodiment, the first video switching signals are transmitted to the display 16, and the display between the first video signals and the second video signals on the display 16 is switched. However, in the third embodiment, any one of the first video signals or the second video signal is transmitted to the display 16 on the basis of the first video switching signals.

Figure 10:
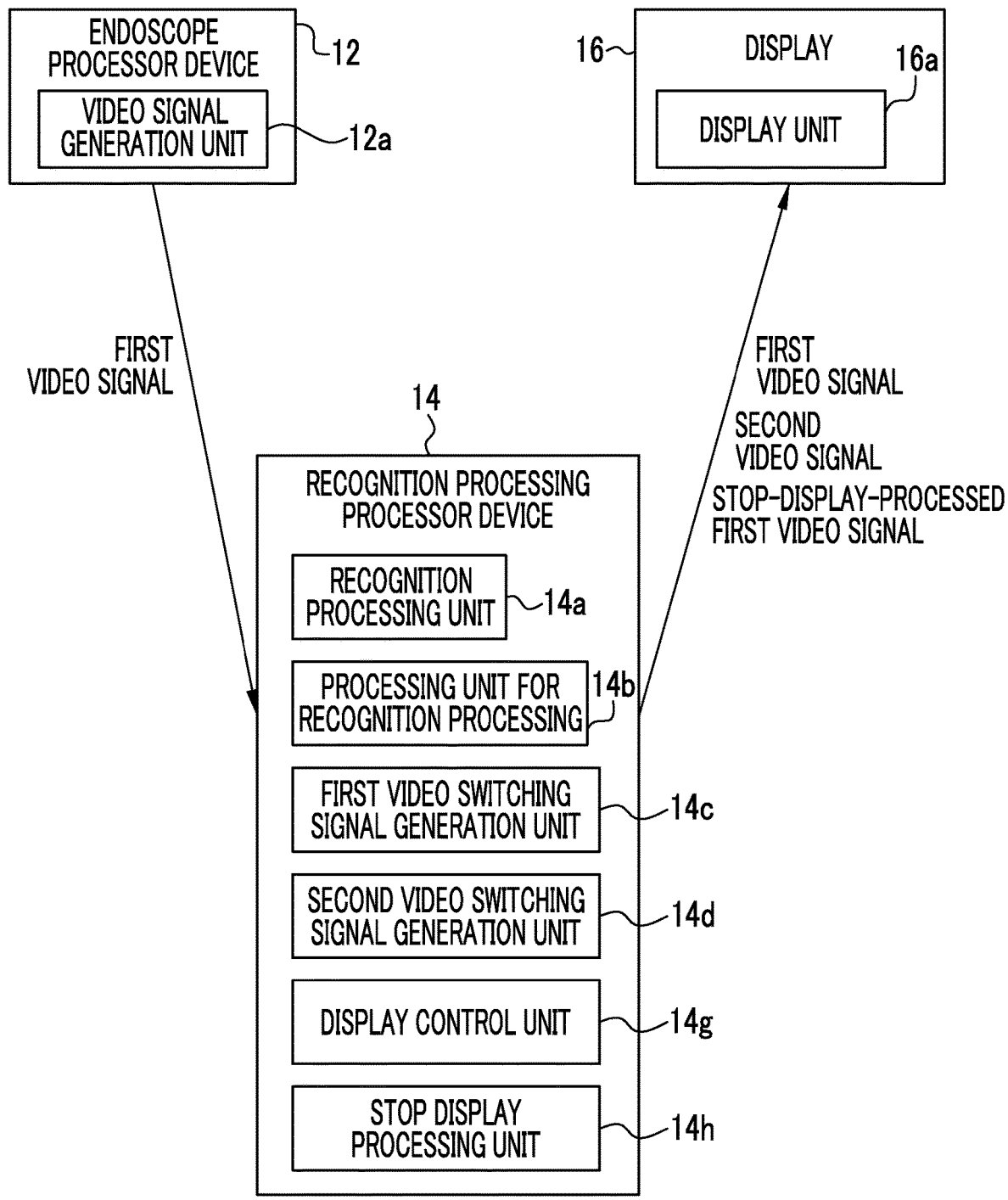
FIG. 10 is a block diagram illustrating a function of a medical image processing system of a third embodiment.

In the third embodiment, as illustrated in FIG. 10, the endoscope processor device 12 has the video signal generation unit 12a that generates the first video signals from the medical image. The recognition processing processor device 14 includes the recognition processing unit 14a, the processing unit for recognition processing 14b, the first video switching signal generation unit 14c that generates the first video switching signals, the second video switching signal generation unit 14d that generates the second video switching signals, a display control unit 14g, and a stop display processing unit 14h. The display 16 includes the display unit 16a. The same reference numerals in the first embodiment and the third embodiment have substantially the same functions in the first embodiment and the third embodiment except for the first video switching signal generation unit 14c and the second video switching signal generation unit 14d.

In the third embodiment, in the recognition processing processor device 14, the display control unit 14g transmits the second video signals to the display 16 in a case where it is determined that the recognition processing is being executed on the basis of the first video switching signals from the first video switching signal generation unit 14c. On the other hand, in a case where it is determined that the recognition processing is being stopped on the basis of the first video switching signals, the display control unit 14g displays the first video signals on the display. Further, in a case where it is determined that the recognition processing is restarted on the basis of the second video switching signals from the second video switching signal generation unit 14d, the display control unit 14g transmits the second video signals to the display.

In the third embodiment, in the display 16, in a case where the second video signals from the recognition processing processor device 14 are received, the second video signals are displayed on the display unit 16a. On the other hand, in the display 16, in a case where, instead of the second video signal, the first video signals are received from the recognition processing processor device 14 due to the stop of the recognition processing, the second video signals are switched to the first video signals so that the first video signals are displayed on the display unit 16a. In the recognition processing processor device 14, in a case where the recognition processing is stopped, the fact that the result display of the recognition processing is being stopped ("AI stopped") is displayed on the display unit 16a (refer to FIG. 4). On the other hand, in a case where the recognition processing is being executed, on the display unit 16a, the display indicating that the result display of the recognition processing is being stopped ("AI stopped") is turned off (refer to FIG. 5).

In the third embodiment, in the recognition processing processor device 14, in a case where the first video signals are displayed on the display unit 16a, the stop display processing unit 14h performs the stop display processing indicating that the result display of the recognition processing is being stopped on the first video signals to generate the stop-display-processed first video signals. The stop-display-processed first video signals are transmitted to the display 16. In the display 16, in a case where the display of the second video signals is switched to the display of the first video signals, the display is switched to the display of the stop-display-processed first video signals.

Note that the merits, demerits, and the like of the first to third embodiments will be described below. In the first embodiment (refer to FIG. 2), even in a case where the recognition processing processor device 14 fails, there is a merit that the first video signals are displayed on the display 16 so that the video is not interrupted. On the other hand, since it is necessary to control the switching of the display between the first video signals and the second video signals on the display 16, there is a demerit that the configuration around the display 16 becomes complicated.

Further, in the second embodiment (refer to FIG. 9), similar to the first embodiment, even in a case where the recognition processing processor device 14 fails, there is a merit that the first video signals are displayed on the display 16 so that the video is not interrupted. On the other hand, the demerit that "the configuration around the display 16 becomes complicated", which is the demerit in the first embodiment, is eliminated, but instead there is a demerit that a connection mechanism capable of transmitting signals other than the first video signals such as the first video switching signals is required between the endoscope processor device 12 and the recognition processing processor device 14.

In the third embodiment (refer to FIG. 10), unlike the first and second embodiments, the video signals transmitted to the display 16 use only one system from the recognition processing processor device 14, and therefore, there is a merit that the connection mechanism is the simplest among the first to third embodiments. On the other hand, there is a demerit that it becomes difficult to transmit appropriate video signals to the display 16 in a case where the recognition processing processor device 14 fails.

Figure 11:
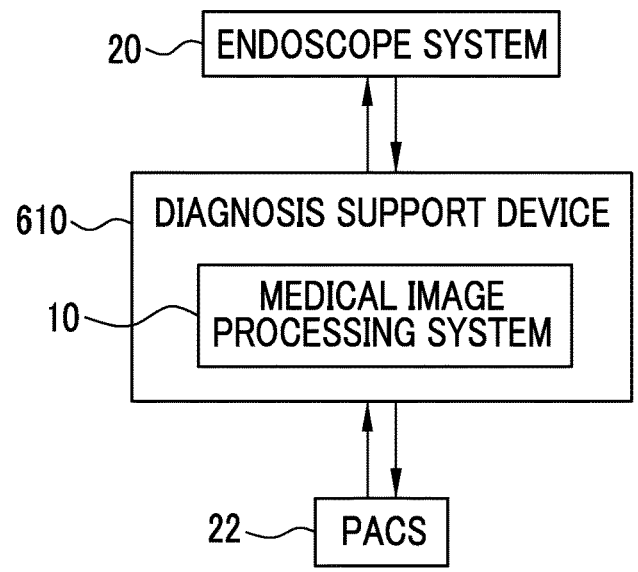
FIG. 11 is a block diagram illustrating a diagnosis support device.
Figure 12:
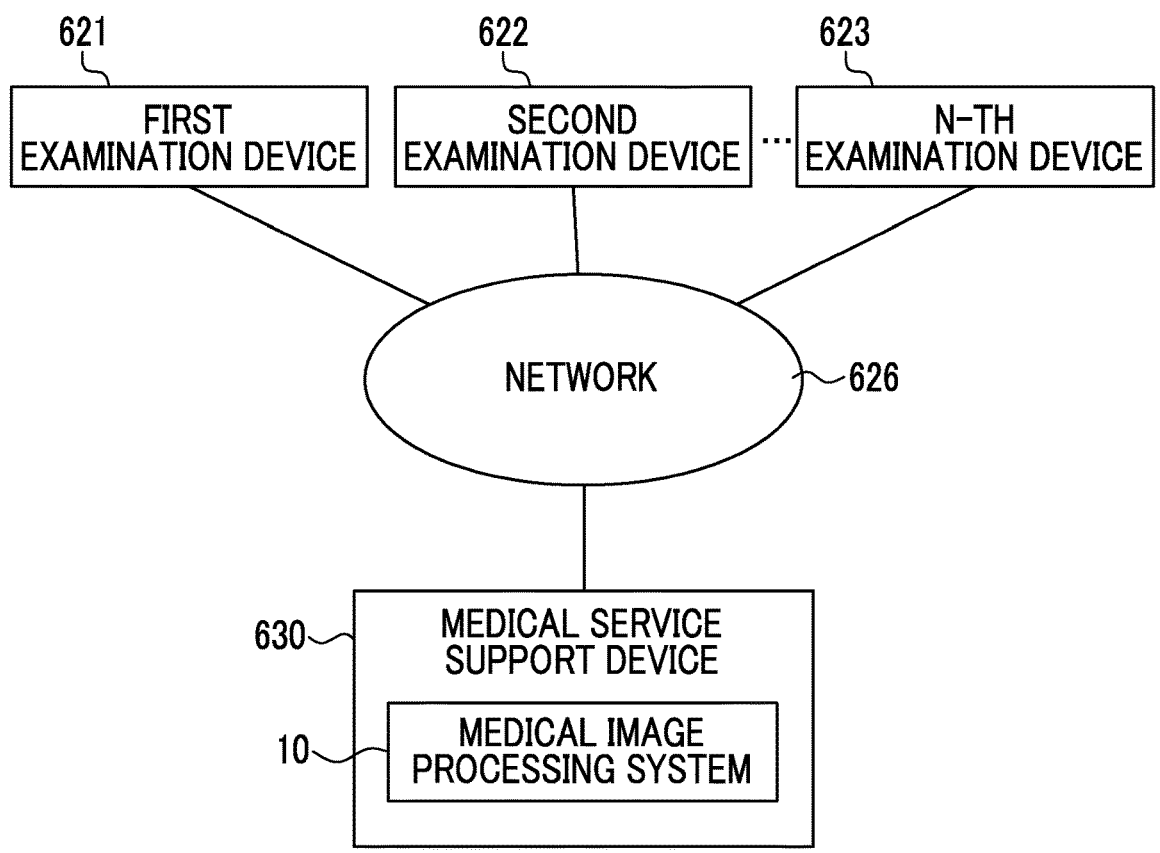
FIG. 12 is a block diagram illustrating a medical service support device.

As illustrated in FIG. 11, a diagnosis support device 610 that is used in combination with the endoscope system 20 and other modalities or picture archiving and communication systems (PACS) can include the medical image processing system 10 in the above-described embodiments and other modifications. As illustrated in FIG. 12, for example, a medical service support device 630 connected via an arbitrary network 626 to various examination devices such as a first examination device 621, a second examination device 622, . . . , and an N-th examination device 633, which include the endoscope system 20 can include the medical image processing system 10 in the above-described embodiments and other modifications.

In addition, various devices or systems including the medical image processing system 10 and the endoscope system 20 can be used with the following various changes and the like.

As the medical image, a normal light image that is obtained from the application of light in a white band or light in a plurality of wavelength ranges as the light in a white band can be used.

In a case where an image that is obtained from the application of light in a specific wavelength range is used as the medical image, a range narrower than the white-light wavelength range can be used as the specific wavelength range.

The specific wavelength range is a blue band or a green band in a visible range, for example.

In a case where the specific wavelength range is a blue band or a green band in the visible range, it is preferable that the specific wavelength range includes a wavelength range of 390 nm to 450 nm or 530 nm to 550 nm, and light in the specific wavelength range has a peak wavelength in a wavelength range of 390 nm to 450 nm or 530 nm to 550 nm.

The specific wavelength range is a red band in the visible range, for example.

In a case where the specific wavelength range is a red band in the visible range, it is preferable that the specific wavelength range includes a wavelength range of 585 nm to 615 nm or 610 nm to 730 nm, and light in the specific wavelength range has a peak wavelength in a wavelength range of 585 nm to 615 nm or 610 nm to 730 nm.

The specific wavelength range can include a wavelength range where a light absorption coefficient in oxyhemoglobin is different from that in reduced hemoglobin, and light in the specific wavelength range can have a peak wavelength in a wavelength range where a light absorption coefficient in oxyhemoglobin is different from that in reduced hemoglobin.

In a case where the specific wavelength range includes a wavelength range where a light absorption coefficient in oxyhemoglobin is different from that in reduced hemoglobin, and light in the specific wavelength range has a peak wavelength in a wavelength range where a light absorption coefficient in oxyhemoglobin is different from that in reduced hemoglobin, it is preferable that the specific wavelength range includes a wavelength range of 400±10 nm, 440±10 nm, 470±10 nm, or 600 nm to 750 nm, and light in the specific wavelength range has a peak wavelength in a wavelength range of 400±10 nm, 440±10 nm, 470±10 nm, or 600 nm to 750 nm.

In a case where the medical image is an in-vivo image of the inside of a living body, the in-vivo image can have information of fluorescence emitted by fluorescent materials in the living body.

Further, as the fluorescence, fluorescence obtained from the application of excitation light, which has a peak wavelength in a range of 390 nm to 470 nm, to the inside of the living body can be used.

In a case where the medical image is the in-vivo image of the inside of the living body, an infrared wavelength range can be used as the specific wavelength range described above.

In a case where the medical image is the in-vivo image of the inside of the living body, and an infrared wavelength range is used as the specific wavelength range, it is preferable that the specific wavelength range includes a wavelength range of 790 nm to 820 nm or 905 nm to 970 nm, and light in the specific wavelength range has a peak wavelength in a wavelength range of 790 nm to 820 nm or 905 nm to 970 nm.

The medical image processing system can include a special light image acquisition unit that acquires a special light image having signals in the specific wavelength range on the basis of a normal light image obtained from the application of light in a white band or light in a plurality of wavelength ranges as the light in a white band. In this case, the special light image can be used as the medical image.

The signals in the specific wavelength range can be obtained from an arithmetic operation based on color information about RGB or CMY included in the normal light image.

A feature amount image generation unit can be provided which generates a feature amount image from an arithmetic operation based on at least one of the normal light image that is obtained from the application of light in a white band or light in a plurality of wavelength ranges as the light in a white band or the special light image that is obtained from the application of light in a specific wavelength range. In this case, the feature amount image can be used as the medical image.

For the endoscope system 20, a capsule endoscope can be used as the endoscope 24. In this case, the light source device 22 and a part of the endoscope processor device 12 can be mounted on the capsule endoscope.

In the above-described embodiments and modifications, for example, the following various processors can be used as the hardware structure of processing units executing various kinds of processing such as the video signal generation unit 12a, the display control unit 12b, the stop display processing unit 12c, the recognition processing unit 14a, the processing unit for recognition processing 14b, the first video switching signal generation unit 14c, the second video switching signal generation unit 14d, the abnormal state detection unit 14e, the operation status recognition unit 14f, the display control unit 14g, the stop display processing unit 14h, and the display control unit 16b. The various processors include a central processing unit (CPU) as a general-purpose processor functioning as various processing units by executing software (program), a programmable logic device (PLD) as a processor of which the circuit configuration can be changed after manufacturing such as a field programmable gate array (FPGA), a dedicated electrical circuit as a processor having a circuit configuration designed exclusively for executing various kinds of processing, and a graphical processing unit (GPU) that performs a large amount of processing such as image processing in parallel.

One processing unit may be configured by one of the various processors, or configured by a combination of the same or different kinds of two or more processors (for example, combination of a plurality of FPGAs, combination of the CPU and the FPGA, or combination of the CPU and the GPU). In addition, a plurality of processing units may be configured by one processor. As an example where a plurality of processing units are configured by one processor, first, there is an aspect where one processor is configured by a combination of one or more CPUs and software as typified by a computer, such as a client or a server, and this processor functions as a plurality of processing units. Second, there is an aspect where a processor fulfilling the functions of the entire system including a plurality of processing units by one integrated circuit (IC) chip as typified by a system on chip (SoC) or the like is used. In this manner, various processing units are configured by using one or more of the above-described various processors as hardware structures.

Furthermore, the hardware structures of the various processors are more specifically electrical circuitry in a form in which circuit elements, such as semiconductor elements, are combined.

EXPLANATION OF REFERENCES

10: medical image processing system
12: endoscope processor device
12a: video signal generation unit
12b: display control unit
12c: stop display processing unit
14: recognition processing processor device
14a: recognition processing unit
14b: processing unit for recognition processing
14c: first video switching signal generation unit
14d: second video switching signal generation unit
14e: abnormal state detection unit
14f: operation status recognition unit
14g: display control unit
14h: stop display processing unit
16: display
16a: display unit
16b: display control unit
20: endoscope system
22: light source device
24: endoscope
30: user interface
610: diagnosis support device
621: first examination device
622: second examination device
623: N-th examination device
626: network
630: medical service support device

What is claimed is:
1. A medical image processing system comprising:
a first processor configured to sequentially acquire medical images, and generate first video signals from the medical images;
a second processor configured to receive the first video signals from the first processor, perform recognition processing on the first video signals, and perform processing for recognition processing for displaying a result of the recognition processing on the first video signals to generate second video signals; and
a display,
wherein the second processor is further configured to generate first video switching signals, and the display displays any one of the second video signals or the first video signals switched from the second video signals on the basis of the first video switching signals, and displays that a result display of the recognition processing is being stopped in a case where the result display of the recognition processing by the second video signals is stopped.

2. The medical image processing system according to claim 1, further comprising:
a third processor provided in the display,
wherein the display receives the first video signals from the first processor, and receives the second video signals from the second processor, and
the third processor is configured to switch the display on the display from the second video signals to the first video signals on the basis of the first video switching signals in a case where the display displays the second video signals.

3. The medical image processing system according to claim 1,
wherein the first processor is further configured to transmit first video priority signals for displaying the first video signals with priority over the second video signals, to the display, in a case where the first video switching signals are received from the second processor,
the display receives any one of the first video signals or the first video priority signals from the first processor, and receives the second video signals from the second processor, and
in a case where the display displays the second video signals, the display on the display is switched from the second video signals to the first video signals on the basis of the first video priority signals.

4. The medical image processing system according to claim 3,
wherein the first processor is further configured to generate stop-display-processed first video signals obtained by performing stop display processing on the first video signals, and transmit the stop-display-processed first video signals to the display as the first video signals, in a case where the display is switched from the second video signals to the first video signals on the basis of the first video priority signals.

5. The medical image processing system according to claim 1,
wherein the second processor is further configured to transmit the second video signals to the display in a case where it is determined that the recognition processing is being executed on the basis of the first video switching signals, and transmit the first video signals to the display in a case where it is determined that the recognition processing is being stopped on the basis of the first video switching signals,
the display displays the second video signals in a case where the second video signals are transmitted from the second processor to the display, and displays the first video signals in a case where the first video signals are transmitted from the second processor to the display.

6. The medical image processing system according to claim 5,
wherein the second processor is further configured to generate stop-display-processed first video signals obtained by performing stop display processing on the first video signals, and transmits the stop-display-processed first video signals to the display as the first video signals, in a case where the first video signals are displayed on the display on the basis of the first video switching signals.

7. The medical image processing system according to claim 1,
wherein the second processor is further configured to stop the recognition processing according to at least one of a stop input for the recognition processing by a user, the recognition process being in an abnormal state, or an operation status by the user being a specific operation status, so that the result display of the recognition processing is stopped by the stop of the recognition processing.

8. The medical image processing system according to claim 7,
wherein the specific operation status includes a treatment operation of the user using a treatment tool.

9. The medical image processing system according to claim 1,
wherein the second processor is further configured to generate second video switching signals in a case where the recognition processing is restarted, and
the display displays the second video signals switched from the first video signals by the second video switching signals.

10. A recognition processing processor device that is connected to a first processor configured to sequentially acquire medical images and generate first video signals from the medical images, and is connected to a display, the recognition processing processor device comprising:
a second processor configured to receive the medical images from the first processor, perform recognition processing on the first video signals, and perform processing for recognition processing for displaying a result of the recognition processing on the first video signals to generate second video signals,
wherein the second processor is further configured to generate first video switching signals, and
any one of the second video signals or the first video signals switched from the second video signals on the basis of the first video switching signals is displayed on the display, and a fact that a result display of the recognition processing is being stopped is displayed on the display in a case where the result display of the recognition processing by the second video signals is stopped.

11. An operation method of a medical image processing system including a first processor configured to sequentially acquire medical images, and generate first video signals from the medical images, a second processor configured to receive the first video signals from the first processor, perform recognition processing on the first video signals, and perform processing for recognition processing for displaying a result of the recognition processing on the first video signals to generate second video signals, and a display, the operation method comprising:
causing the second processor to generate first video switching signals; and
causing the display to display any one of the second video signals or the first video signals switched from the second video signals on the basis of the first video switching signals, and to display that a result display of the recognition processing is being stopped in a case where the result display of the recognition processing by the second video signals is stopped.

* * * * *